United States Patent [19]

Welch, Jr.

[11] 4,434,173

[45] Feb. 28, 1984

[54] BIS-ESTERS OF 4,5-DI(HYDROXYMETHYL)-2-OXO-1,3-DIOXOLE AS ANTIBACTERIAL AGENTS

[75] Inventor: Willard M. Welch, Jr., Mystic, Conn.

[73] Assignee: Pfizer Inc., New York, N.Y.

[21] Appl. No.: 441,980

[22] Filed: Nov. 15, 1982

Related U.S. Application Data

[63] Continuation-in-part of Ser. No. 410,762, Aug. 23, 1982, abandoned.

[51] Int. Cl.$^3$ .................... A61K 31/43; C07D 499/32; C07D 317/40; C07D 499/00
[52] U.S. Cl. ................................ 424/271; 260/239.1; 260/245.2 R; 549/229
[58] Field of Search ..................... 260/239.1, 245.2 R; 424/271; 549/229

[56] References Cited

U.S. PATENT DOCUMENTS

| | | | |
|---|---|---|---|
| 4,234,579 | 11/1980 | Barth | 424/246 |
| 4,244,951 | 1/1981 | Bigham | 424/250 |
| 4,342,693 | 8/1982 | Sakamoto et al. | 549/229 |
| 4,351,840 | 9/1982 | Pirie | 424/271 |
| 4,359,472 | 11/1982 | Hamanaka | 424/271 |
| 4,389,408 | 6/1983 | Sakamoto et al. | 424/271 |

FOREIGN PATENT DOCUMENTS 39086 11/1981 European Pat. Off. .

*Primary Examiner*—Natalie Trousof
*Assistant Examiner*—Vera C. Clarke
*Attorney, Agent, or Firm*—Charles J. Knuth; Albert E. Frost; J. Trevor Lumb

[57] ABSTRACT

Derivatives of 4,5-di(hydroxymethyl)-2-oxo-1,3-dioxole in which one hydroxy group has been esterified through the carboxy group of ampicillin or amoxicillin, and the other hydroxy group has been esterified through the carboxy group of sulbactam (penicillanic acid 1,1-dioxide), are useful as antibacterial agents. Certain novel compounds, which are useful as intermediates to the aforesaid antibacterial agents, are also disclosed.

15 Claims, No Drawings

BIS-ESTERS OF 4,5-DI(HYDROXYMETHYL)-2-OXO-1,3-DIOXOLE AS ANTIBACTERIAL AGENTS

CROSS-REFERENCE TO RELATED APPLICATION

This application is a continuation-in-part of application Ser. No. 410,762, filed Aug. 23, 1982, and now abandoned.

BACKGROUND OF THE INVENTION

This invention relates to new chemical compounds. More particularly it relates to new chemical compounds which are of value as antibacterial agents. These new antibacterial agents are bis-esters of 4,5-di(hydroxymethyl)-2-oxo-1,3-dioxole, in which one hydroxy group has been esterified with the carboxy group of 6-(2-amino-2-phenylacetamido)penicillanic acid (ampicillin) or 6-(2-amino-2-[4-hydroxyphenyl]acetamido)penicillanic acid (amoxicillin), and the other hydroxy group has been esterified with the carboxy group of penicillanic acid 1,1-dioxide (sulbactam).

European patent application No. 39,086, published Nov. 4, 1981, discloses esters of 4-hydroxymethyl-2-oxo-1,3-dioxole, optionally further substituted at the 5-position, in which the hydroxy group has been esterified with the carboxy group of 6-(2-amino-2-phenylacetamino)penicillanic acid. U.S. Pat. No. 4,244,951 discloses bis-esters of methanediol in which one hydroxy group has been esterified with the carboxy group of certain 6-acrylaminopenicillanic acids and the other hydroxy group has been esterified using penicillanic acid 1,1-dioxide. In like manner, U.S. Pat. No. 4,359,472 discloses bis-esters of di(hydroxymethyl) carbonate with certain 6-acrylaminopenicillanic acid compounds and penicillanic acid 1,1-dioxide. Penicillanic acid 1,1-dioxide is known from U.S. Pat. No. 4,234,579 as an antibacterial agent and beta-lactamase inhibitor.

The antibacterial agents of the present invention are efficiently absorbed from the gastrointestinal tract of mammals, and after absorption they are transformed into 6-(2-amino-2-phenylacetamido)penicillanic acid (ampicillin) or 6-(2-amino-2-[4-hydroxyphenyl]acetamido)penicillanic acid (amoxicillin) and penicillanic acid 1,1-dioxide (sulbactam).

SUMMARY OF THE INVENTION

This invention provides new antibacterial agents of the formula

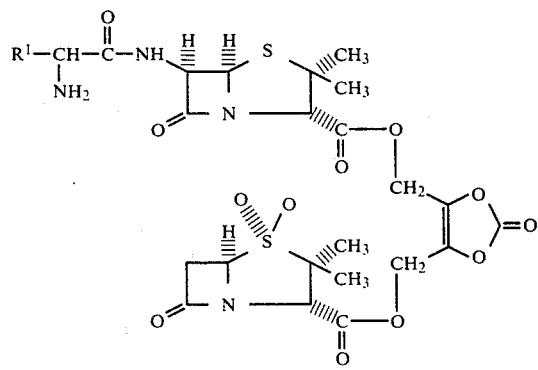

and the pharmaceutically-acceptable acid-addition salts thereof; wherein $R^1$ is selected from the group consisting of phenyl and 4-hydroxyphenyl.

Also, this invention embraces a method of treating a bacterial infection in a mammalian subject which comprises administering thereto an antibacterially effective amount of a compound of formula I.

Yet further this invention embraces pharmaceutical compositions, suitable for treating a bacterial infection in a mammalian subject, which comprises an antibacterially effective amount of a compound of formula I and a pharmaceutically-acceptable carrier.

DETAILED DESCRIPTION OF THE INVENTION

This invention relates to derivatives of penicillanic acid, which is represented by the following structural formula

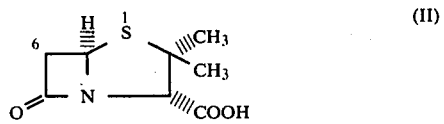

In formula II, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration.

Additionally, the compounds of formula I are derivatives of 4,5-dimethyl-2-oxo-1,3-dioxole, which is the compound of the formula

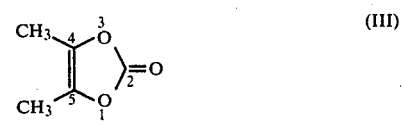

Accordingly, the compounds of formula I are named as derivatives of 4-(penicillanoyloxymethyl)-5-(1,1-dioxopenicillanoyloxymethyl)-2-oxo-1,3-dioxole (IV).

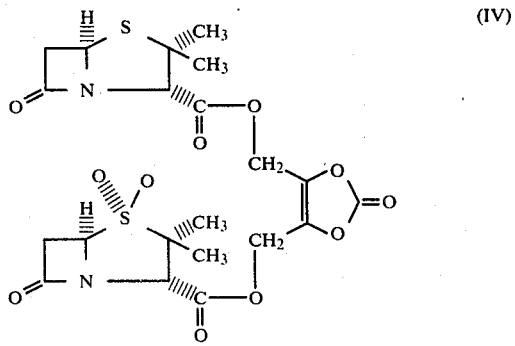

The compound of formula III is named 4,5-dimethyl-1,3-dioxolen-2-one in published European patent application No. 39,086.

Moreover, throughout this specification, whenever reference is made to a compound which has a 2-amino-2-(substituted)acetamido or 2-(substituted amino)-2-(substituted)acetamido group at the 6-position of a penicillanic acid derivative, it is to be understood that this refers to a compound in which said 2-amino-2-(substituted)acetamido or 2-(substituted amino)-2-(substituted)acetamido has the D-configuration.

The compounds of formula I can be prepared by reacting a compound of the formula

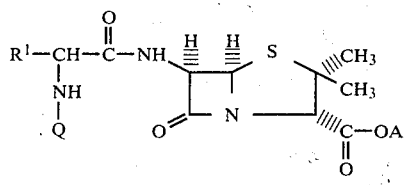

(V)

with a compound of the formula

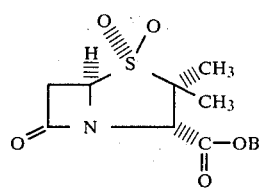

(VI)

wherein $R^1$ is phenyl or 4-hydroxyphenyl, Q is an amino protecting group, and A and B are each selected from the group consisting of M and a group of the formula

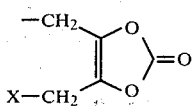

(VII)

wherein

M is a carboxylate salt forming cation and X is a good leaving group;

provided that when A or B is M then the other of A and B is of formula VII, and when A or B is of formula VII the other of A and B is M;

to give a compound of the formula

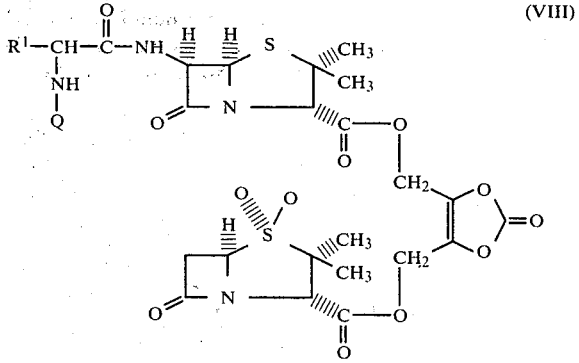

(VIII)

followed by removal of the protecting group Q. Useful groups for Q are 1-methyl-2-alkoxycarbonylvinyl groups such as the 1-methyl-2-methoxycarbonylvinyl group; useful leaving groups for X are halogen atoms, such as chloro, bromo and iodo; and, when A or B is M, useful carboxylate salts for compound V or VI are alkali metal salts, such as sodium and potassium salts; alkaline earth metal salts, such as calcium and barium salts; tertiary amine salts, such as trimethylamine, triethylamine, tributylamine, diisopropylethylamine, N-methylmorpholine, N-methylpiperidine, N-methylpyrrolidine and N,N-dimethylpiperazine salts; and tetraalkylammonium salts, such as tetramethylammonium and tetra-n-butylammonium salts.

The reaction between a compound of the formula V and a compound of formula VI is usually carried out by contacting the reagents in a reaction-inert, organic solvent, at a temperature in the range from 0° to 80° C., and preferably from 30° to 60° C. The compounds of formulae V and VI are normally contacted in equimolar proportions, but an excess of either compound can be used. A wide variety of solvents can be used, and typical solvents are low-molecular weight ketones, such as acetone and methyl ethyl ketone, N,N-dimethylformamide, N,N-dimethylacetamide, N-methylpyrrolidone, dimethyl sulfoxide and hexamethylphosphoramide. The reaction temperature varies according to a number of factors, but at about 55° C. reaction times of a few hours, e.g. 2 to 4 hours are commonly used.

The compound of formula VIII can be isolated by conventional methods. For example, the reaction mixture can be filtered and then the solvent removed by evaporation in vacuo. The residue is then partitioned between water and a water-immiscible, volatile, organic solvent, such as ethyl acetate, and the layers are separated. The ethyl acetate layer is dried and evaporated to afford the compound of formula VIII.

The compound of formula VIII can be purified, if desired, by conventional methods such as recrystallization or chromatography; alternatively, the protecting group Q can be removed from the crude product.

The protecting group Q is removed from a compound of formula VIII by a conventional method for that particular protecting group, but due regard must be given to the lability of the beta-lactam rings.

The 1-methyl-2-alkoxycarbonylvinyl groups can be removed simply by exposing the compound of formula VIII to an aqueous or partially aqueous solvent system at an acidic pH, i.e. a pH from 0.5 to 3. This is conveniently achieved by treating the compound of formula VIII with water and 1 equivalent of a strong acid, optionally in the presence of a co-solvent, at a temperature in the range from −10° to 30° C. Typical examples of strong acids which can be used are hydrochloric acid, hydrobromic acid, perchloric acid, sulfuric acid, nitric acid and sulfonic acids, such as methanesulfonic acid, benzenesulfonic acid, toluenesulfonic acids and naphthalenesulfonic acids. A variety of co-solvents can be used, the major requirements of such a solvent being that it is at least partially miscible with water and it does not adversely affect either the starting material or the product. Typical co-solvents are low molecular weight ketones, such as acetone and low molecular weight ethers, such as tetrahydrofuran and 1,2-dimethoxyethane. The reaction is usually complete within an hour, and the product is isolated by conventional methods. In many instances, it is sufficient simply to remove the co-solvent by evaporation in vacuo and remove the alkyl acetoacetate by extraction with a water-immiscible solvent such as diethyl ether. In a typical procedure, the compound of formula VIII is treated with one equivalent of hydrochloric acid in aqueous acetone. The reaction is usually complete within a short time, e.g. within one hour. Then the acetone is removed by evaporation in vacuo, and the alkyl acetoacetate by-product is removed by extraction with ether. Finally, the compound of formula I is isolated by partitioning the residue between a volatile, water-immiscible organic solvent, such as dichloromethane, and saturated sodium chloride solution. Separation of the layers, followed by drying and evaporating the organic layer, affords the compound of formula I as its hydrochloride salt.

The hydrochloride salt of the compound of formula I can be converted into the corresponding free base compound by standard methods for penicillin compounds. For example, the hydrochloride salt can be reacted with one molar equicalent of sodium bicarbonate in a two-phase system of water and dichloromethane. Separation of the layers, followed by evaporation of dichloromethane, affords the free base compound.

The compounds of formula I will form acid-addition salts other than the hydrochloride salt, and all of the acid-addition salts of compounds of the formula I are to be considered to be within the scope and purview of this invention. Said acid addition salts are prepared by standard methods for penicillin compounds, for example by combining a solution of the compound of formula I in a suitable solvent (e.g. water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate, benzenesulfonate, 4-toluenesulfonate and 2-naphthalenesulfonate salts.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of the formula I and the salts thereof, can be purified by conventional methods for penicillin compounds, e.g. recrystallization or chromatography, but due regard must be given to the lability of the beta-lactam ring systems.

The compounds of formula V, wherein A is of formula VII, can be prepared by reaction of a compound of the formula V, wherein A is M, with a compound of the formula

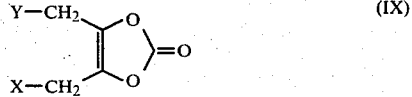

wherein $R^1$, Q, M and X are as previously defined, and Y is a good leaving group, with the proviso that Y is the same as X or a better leaving group than X. Useful leaving groups for Y are chloro, bromo and iodo. The reaction can be carried out using the same conditions as described earlier for the reaction of a compound of formula V with a compound of formula VI.

In like manner, the compounds of formula VI, wherein B is of formula VII, can be prepared by reaction of a compound of formula VI, wherein B is M, with a compound of formula IX, wherein $R^1$, Q, M, X and Y are as previously defined. This reaction can be carried out using the same conditions as described earlier for the reaction of a compound of the formula V with a compound of formula VI.

The compounds of formula IX are prepared from the appropriate compound of the formula

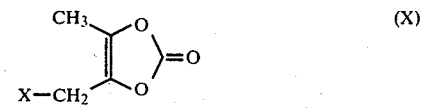

by standard methods. When Y is chloro, bromo or iodo, the compound of formula X is halogenated using standard procedures, typical halogenating agents being N-chlorosuccinimide, N-bromosuccinimide, chlorine, bromine and t-butyl hypoiodite. When X is bromo, a particularly useful halogenating system is N-bromosuccinimide in carbon tetrachloride. See further published European patent application No. 39,477.

The compounds of formula, wherein A is M, and the compounds of formula VI, wherein B is M, can be prepared by the known methods, or methods analogous to known methods. See, for example, U.S. Pat. Nos. 4,234,579, 3,674,776 (Re 28,744) and 3,325,479.

The compounds of formula I possess in vivo antibacterial activity in mammals, and this activity can be demonstrated by standard techniques for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula I. The compounds of formula I can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

A compound of formula I breaks down to 6-(2-amino-2-phenylacetamido)penicillanic acid (ampicillin) and penicillanic acid 1,1-dioxide (sulbactam), or 6-(2-amino-2-[4-hydroxyphenyl]acetamido)penicillanic acid (amoxicillin) and penicillanic acid 1,1-dioxide (sulbactam), after administration to a mammalian subject by both the oral and parenteral route. Sulbactam then functions as a beta-lactamase inhibitor, and it increases the antibacterial effectiveness of the ampicillin or amoxicillin. Thus the compounds of the formula I will find use in the control of bacteria which are susceptible to a 1:1 mixture of ampicillin and sulbactam, or amoxicillin and sulbactam, e.g. susceptible strains of *Escherichia coli* and *Staphylococcus aureus*.

In determining whether a particular strain of *Escherichia coli* or *Staphylococcus aureus* is sensitive to a particular compound of formula I, the in vivo test described earlier can be used. Alternatively, the minimum inhibitory concentration (MIC) of a 1:1 mixture of ampicillin and sulbactam, or amoxicillin and sulbactam, can be measured. The MIC's can be measured by the procedure recommended by the International Collaborative Study on Antibiotic Sensitivity Testing (Ericcson and Sherris, *Acta. Pathologica et Microbiologia Scandinav,* Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve two-fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. However, weight ratios in the range from 1:4 to 4:1 can conveniently be used. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from 20 to about 100 mg per kilogram of body weight per day, and parenterally at dosages from about 10 to about 100 mg per kilogram of body weight per day, usually in divided doses. In some instances it may be necessary to use doses outside these ranges.

The following examples and preparations are provided solely for further illustration. Nuclear magnetic resonance (NMR) spectra were measured for solutions in deuterated chloroform ($CDCl_3$) or deuterated dimethyl sulfoxide (DMSO-$d_6$), and peak positions are reported in parts per million downfield from tetramethylsilane. The following abbreviations for peak shapes are used: s, singlet; d, doublet; m, multiplet. Infrared (IR) spectra were measured as potassium bromide discs.

EXAMPLE 1

4-(6-[2-Amino-2-phenylacetamido]penicillanoyloxymethyl)-5-(1,1-dioxopenicillanoyloxymethyl)-2-oxo-1,3-dioxole Hydrochloride To a stirred solution of 600 mg of 4-(6-[2-(1-methyl-2-methoxycarbonylvinylamino)-2-phenylacetamido]-penicillanoyloxymethyl)-5-(1,1-dioxopenicillanoyloxymethyl)-2-oxo-1,3-dioxole in 25 ml of acetone was added 9.1 ml of 0.1 N hydrochloric acid. Stirring was continued for 20 minutes at room temperature, and then the acetone was removed by evaporation in vacuo. The residual aqueous layer was washed twice with diethyl ether, and then dichloromethane was added. The aqueous phase was saturated with sodium chloride and the layers were separated. The dichloromethane layer was dried ($Na_2SO_4$) and then 20 ml of isopropanol was added. The solution thus obtained was concentrated to small volume in vacuo and the white solid which precipitated was collected by filtration. This afforded 252 mg of the title compound.

The IR spectrum (KBr disc) showed absorptions at 5.46, 5.58, 5.66 and 5.9 microns. The NMR spectrum (DMSO-$d_6$) of the title compound showed absorptions at 1.34 (3H, s), 1.36 (3H, s), 1.47 (3H, s), 1.48 (3H, s), 3.22–3.42 (2H, m), 3.71 (1H, d of d, J=4, 16), 4.43 (1H, s), 4.52 (1H, s), 4.97 (1H, s), 5.22 (1H, m), 5.24 (2H, s), 5.29 (2H, s), 5.48 (1H, d, J=4), 5.58 (1H, d, J=4), 7.49–7.54 (5H, m), 7.97 (2H, broad s) and 9.31 (1H, broad s) ppm downfield from tetramethylsilane.

EXAMPLE 2

4-(6-[2-Amino-2-(4-hydroxyphenyl)acetamido]penicillanoyloxymethyl)-5-(1,1-dioxopenicillanoyloxymethyl)-2-oxo-1,3-dioxole Hydrochloride The title compound can be prepared by hydrolysis of 4-(6-[2-(1-methyl-2-methoxycarbonylvinylamino)-2-(4-hydroxyphenyl)acetamido]penicillanoyloxymethyl)-5-(1,1-dioxopenicillanoyloxymethyl)-2-oxo-1,3-dioxole using 0.1 N hydrochloric acid, according to the procedure of Example 1.

EXAMPLE 3

4-(6-[2-Amino-2-phenylacetamido]penicillanoyloxymethyl)-5-(1,1-dioxopenicillanoyloxymethyl)-2-oxo-1,3-dioxole To 729 mg of 4-(6-[2-amino-2-phenylacetamido]-penicillanoyloxymethyl)-5-(1,1-dioxopenicillanoyloxymethyl)-2-oxo-1,3-dioxole hydrochloride is added 30 ml of dichloromethane and 30 ml of water in which has been dissolved 84 mg of sodium bicarbonate. The mixture is shaken for 1 minute and then the layers are separated. The dichloromethane layer is dried ($Na_2SO_4$), and then it is evaporated in vacuo to afford the title compound.

EXAMPLE 4

4-(6-[2-(1-Methyl-2-methoxycarbonylvinylamino)-2-phenylacetamido]penicillanoyloxymethyl)-5-(1,1-dioxopenicillanoyloxymethyl)-2-oxo-1,3-dioxole To a stirred solution of 1.15 g of 4-(6-[2-(1-methyl-2-methoxycarbonylvinylamino)-2-phenylacetamido]-penicillanoyloxymethyl)-5-bromomethyl-2-oxo-1,3-dioxole in 25 ml of acetone was added 457 mg of sodium penicillanate 1,1-dioxide followed by 580 mg of tetra-n-butylammonium bromide. The resulting suspension was heated under reflux for 3.5 hours and then it was filtered hot. The resulting solution was cooled and evaporated in vacuo, and the residue was partitioned between ethyl acetate and water. The organic phase was washed with saturated sodium chloride solution, water and again saturated sodium chloride solution, and then it was dried and evaporated in vacuo. The residue was chromatographed on silica gel to give 600 mg of the title compound.

EXAMPLE 5

4-(6-[2-(1-Methyl-2-methoxycarbonylvinylamino)-2-(4-hydroxyphenyl)acetamido]penicillanoyloxymethyl)-5-(1,1-dioxopenicillanoyloxymethyl)-2-oxo-1,3-dioxole The title compound can be prepared by coupling 4-(6-[2-(1-methyl-2-methoxycarbonylvinylamino)-2-(4-hydroxyphenyl)acetamido]penicillanoyloxymethyl)-5-bromomethyl-2-oxo-1,3-dioxole with sodium penicillanate 1,1-dioxide according to the procedure of Example 4.

EXAMPLE 6

4-(6-[2-(1-Methyl-2-propoxycarbonylvinylamino)-2-phenylacetamido]penicillanoyloxymethyl)-5-(1,1-dioxopenicillanoyloxymethyl)-2-oxo-1,3-dioxole The title compound can be prepared by coupling 4-(6-[2-(1-methyl-2-propoxycarbonylvinylamino)-2-phenylacetamido]penicillanoyloxymethyl)-5-bromomethyl-2-oxo-1,3-dioxole with sodium penicillanate 1,1-dioxide according to the procedure of Example 4.

EXAMPLE 7

4-(6-[2-(1-Methyl-2-methoxycarbonylvinylamio)-2-phenylacetamido]penicillanoyloxymethyl)-5-(1,1-dioxopenicillanoyloxymethyl)-2-oxo-1,3-dioxole The title compound can be prepared by coupling sodium 6-(2-[1-methyl-2-methoxycarbonylvinylamino]-2-phenylacetamido)penicillanate with 4-(1,1-dioxopenicillanoyloxymethyl)-5-bromomethyl-2-oxo-1,3-dioxole according to the procedure of Example 4.

EXAMPLE 8

4-(6-[2-(1-Methyl-2-methoxycarbonylvinylamino)-2-phenylacetamido]penicillanoyloxymethyl)-5-bromomethyl-2-oxo-1,3-dioxole To a stirred suspension of 4.78 g of the tetra-n-butylammonium salt of 6-(2-[1-methyl-2-methoxycarbonylvinylamino]-2-phenylacetamido)penicillanic acid in 100 ml of acetone was added 1.72 g of 4,5-di(bromomethyl)-2-oxo-1,3-dioxole at 5° C. Stirring was continued for 5 minutes at 5° C. and then the reaction mixture was allowed to warm to room temperature. Stirring was continued at room temperature for 30 minutes, and then the reaction mixture was decolorized with activated carbon and evaporated in vacuo. The residue was chromatographed on silica gel to give 1.15 g of the title compound.

EXAMPLE 9

4-(6-[2-(1-Methyl-2-methoxycarbonylvinylamino)-2-(4-hydroxyphenyl)acetamido]penicillanoyloxymethyl)-5-bromomethyl-2-oxo-1,3-dioxole The title compound can be prepared by reaction of the tetra-n-butylammonium salt of 6-(2-[1-methyl-2-methoxycarbonylvinylamino]-2-[4-hydroxyphenyl]acetamido)penicillanic acid with 4,5-di(bromomethyl)-2-oxo-1,3-dioxole, according to the procedure of Example 8.

EXAMPLE 10

4-(6-[2-(1-Methyl-2-propoxycarbonylvinylamino)-2-phenylacetamido]penicillanoyloxymethyl)-5-bromomethyl-2-oxo-1,3-dioxole The title compound can be prepared by reaction of the tetra-n-butylammonium salt of 6-(2-[1-methyl-2-propoxycarbonylvinylamino]-2-phenylacetamido)-penicillanic acid with 4,5-di(bromomethyl)-2-oxo-1,3-dioxole, according to the procedure of Example 8.

EXAMPLE 11

4-(1,1-Dioxopenicillanoyloxymethyl)-5-bromomethyl-2-oxo-1,3-dioxole

The title compound can be prepared by reaction of the tetra-n-butylammonium salt of penicillanic acid 1,1-dioxide with 4,5-di(bromomethyl)-2-oxo-1,3-dioxide, according to the procedure of Example 8.

EXAMPLE 12

4,5-Di(bromomethyl)-2-oxo-1,3-dioxole

To a stirred solution of 1.22 g of 4-bromomethyl-5-methyl-2-oxo-1,3-dioxole in 30 ml of carbon tetrachloride was added 1.125 g of N-bromosuccinimide. The resulting solution was heated under reflux and irradiated for 15 minutes. The reaction mixture was filtered hot, cooled, and then evaporated in vacuo to give the title product as a yellow oil.

PREPARATION 1

4-Bromomethyl-5-methyl-2-oxo-1,3-dioxole

To a stirred solution of 3.0 g of 4,5-dimethyl-2-oxo-1,3-dioxole in 100 ml of carbon tetrachloride was added 4.63 g of N-bromosuccinimide. The resulting solution was heated under reflux and irradiated for 15 minutes. The reaction mixture was cooled to 0°–5° C., filtered and evaporated to give the title product.

The NMR spectrum (CDCl$_3$) showed absorptions at 2.05 (5% of starting material), 2.18 (3H, s), 4.30 (2H, s) and 4.35 (5% of dibromo compound) ppm downfield from tetramethylsilane. The IR spectrum showed an absorption at 5.49 microns.

PREPARATION 2

4,5-Dimethyl-2-oxo-1,3-dioxole

A solution of phosgene (12.18 g) in cold dichloromethane was added dropwise to a cold solution of 3-hydroxy-2-butanone (10.83 g) and 16.38 g of N,N-dimethylaniline in 50 ml dichloromethane. The resulting green solution was stirred 2 hours at 0°–5° C. The solution was then evaporated to give an oil which was heated at 160°–190° C. for 30 minutes. The cooled reaction mixture was partitioned between water and ether. The separated aqueous layer was further extracted with ether and the combined organic extracts were dried and concentrated. The residue was triturated with pentane to give 3.53 g (25%) of a white crystalline solid, m.p. 76°–78° C.

The NMR spectrum of the product (CDCl₃) showed an absorption at 2.05 (s) ppm downfield from tetramethylsilane. The mass spectrum showed peaks at m/e 114, 56 and 43 (100%).

I claim:
1. A compound of the formula

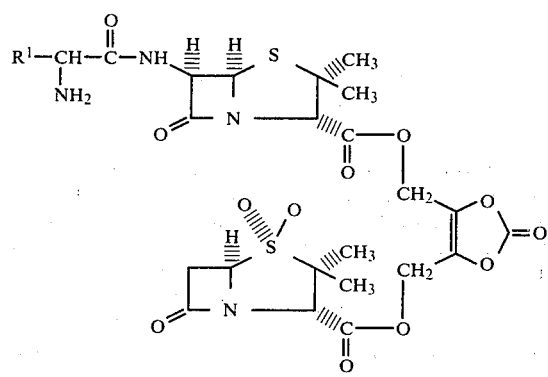

and the pharmaceutically-acceptable acid-addition salts thereof;
wherein $R^1$ is selected from the group consisting of phenyl and 4-hydroxyphenyl.

2. The compound according to claim 1, wherein $R^1$ is phenyl.

3. A method of treating a bacterial infection in a mammalian subject, which comprises administering thereto an antibacterially effective amount of a compound of the formula

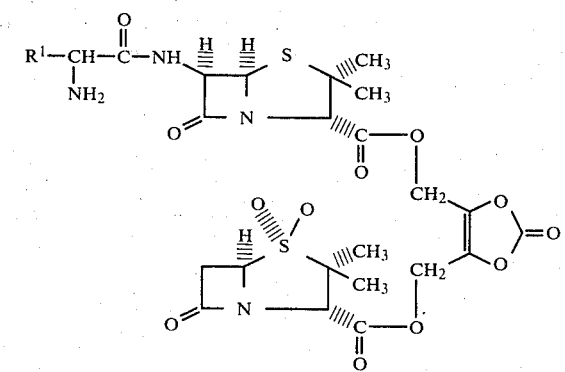

or a pharmaceutically-acceptable acid-addition salt thereof;
wherein $R^1$ is selected from the group consisting of phenyl and 4-hydroxyphenyl.

4. The method according to claim 3, wherein $R^1$ is phenyl.

5. A pharmaceutical composition suitable for treating a bacterial infection in a mammalian subject which comprises an antibacterially-effective amount of a compound according to claim 1 and pharmaceutically-acceptable carrier, in a weight ratio in the range from 1:4 to 4:1.

6. A compound of the formula

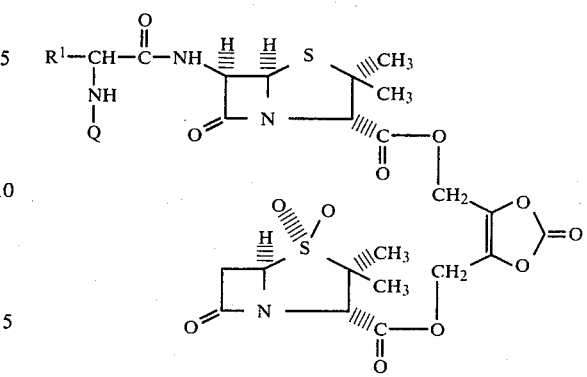

wherein $R^1$ is selected from the group consisting of phenyl and 4-hydroxyphenyl, and Q is 1-methyl-2-alkoxycarbonylvinyl having 1 to 3 carbons in said alkoxy.

7. A compound according to claim 6, wherein $R^1$ is phenyl.

8. The compound according to claim 7, wherein Q is 1-methyl-2-methoxycarbonylvinyl.

9. A compound of the formula

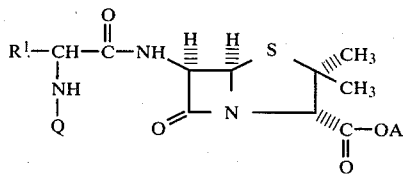

wherein $R^1$ is selected from the group consisting of phenyl and 4-hydroxyphenyl, Q is 1-methyl-2-alkoxycarbonylvinyl having 1 to 3 carbons in said alkoxy and A is

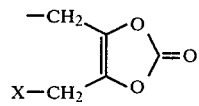

wherein X is selected from the group consisting of chloro, bromo and iodo.

10. A compound according to claim 9, wherein X is bromo.

11. A compound according to claim 10, wherein $R^1$ is phenyl.

12. The compound according to claim 11, wherein Q is 1-methyl-2-methoxycarbonylvinyl.

13. A compound of the formula

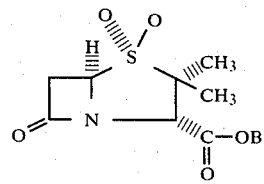

wherein B is

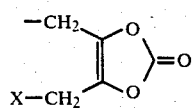
wherein X is selected from the group consisting of chloro, bromo and iodo.
14. The compound according to claim 13, wherein X is bromo.
15. The compound of the formula
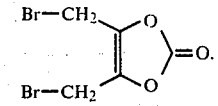
* * * * *